United States Patent [19]

Jackman et al.

[11] Patent Number: 4,946,995

[45] Date of Patent: * Aug. 7, 1990

[54] PROCESS FOR THE PRODUCTION OF THIOCARBOHYDRAZIDE

[75] Inventors: Dennis E. Jackman, Prairie Village, Kans.; Gary W. Combs, Blue Springs, Mo.; Westphal Dietmar B., Remscheid, Fed. Rep. of Germany

[73] Assignee: Mobay Corporation, Pittsburgh, Pa.

[*] Notice: The portion of the term of this patent subsequent to Jul. 10, 2007 has been disclaimed.

[21] Appl. No.: 325,403

[22] Filed: Mar. 17, 1989

[51] Int. Cl.$^5$ .......................................... C07C 241/02
[52] U.S. Cl. ...................................................... 564/18
[58] Field of Search ............................... 564/18; 562/28

[56] References Cited

U.S. PATENT DOCUMENTS 2,726,263 12/1955 Audrieth et al. ................... 260/552
3,198,698 8/1965 Reuter et al. .......................... 167/22
4,172,092 10/1979 Malone ........................... 260/552 SC
4,294,985 10/1981 Cramm et al. ......................... 564/18

OTHER PUBLICATIONS

Guha et al., Journal of Chem. Soc., 125, pp. 1215, 1924.

Primary Examiner—Richard L. Raymond
Assistant Examiner—Peter G. O'Sullivan
Attorney, Agent, or Firm—Joseph C. Gil; Lyndanne M. Whalen

[57] ABSTRACT

TCH is produced by a process which does not require expensive measures to remove hydrazine. In this process, hydrazinium dithiocarbazinate is reacted with an amine other than hydrazine or a strong base, optionally in the presence of water. It is preferred that a sulfur suppressing compound also be included in the reaction mixture. The precipitated TCH is removed from the reaction mixture to leave a mother liquor. Hydrazinium-dithiocarbazinate may then be added to the mother liquor. TCH precipitates and may be readily recovered.

9 Claims, No Drawings

PROCESS FOR THE PRODUCTION OF THIOCARBOHYDRAZIDE

BACKGROUND OF THE INVENTION

The present invention relates to an improved process for the production of thiocarbohydrazide.

Several processes for the manufacture of thiocarbohydrazide (TCH) are known. TCH may be obtained during the hydrazinolysis of thiophosgene in moderate yields using ether or water as the reaction medium. It is also known to manufacture TCH by hydrazinolysis of diethylxanthate (Guha et al., J. Chem. Soc. 125, 1215 (1924)). Simply heating the two reaction components in the absence of a solvent results in yields of 70–74% of theory. (Beyer et al., Ber. 87, 1401 (1954)).

It is also known to prepare thiocarbohydrazide through conversion of dialkyltrithiocarbonates with hydrazine. Cyclic trithiocarbonate may also be used for this synthesis. Ethylenetrithiocarbonate, for example, generally gives pure thiocarbohydrazide in a yield of about 71% of theory. The hydrazinolysis of methyldithiocarbazinate typically leads to a yield of 65% of theory of thiocarbohydrazide.

The most common synthesis of thiocarbohydrazide is, however, the conversion of carbon disulfide with hydrazine. Hydrazinium-dithiocarbazinate (HDTC) forms according to equation (1):

$$CS_2 + 2H_2NNH_2 \rightarrow H_2NNHCSSH \cdot NH_2NH_2 \quad (1)$$

This compound is then converted to thiocarbohydrazide with evolution of hydrogen sulfide according to equation (2):

$$H_2NNHCSSH \cdot NH_2NH_2 \rightarrow H_2NNHCSNHNH_2 + H_2S \quad (2)$$

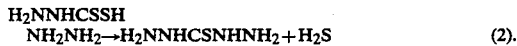

Better yields and pure product are obtained when the hot aqueous solution of the hydrazinium-dithiocarbazinate is digested with lead oxide (Stolle, et al., Ber. 41, 1099 (1908)).

The yields of thiocarbohydrazide can also be increased when conducting the decomposition of hydrazinium-dithiocarbazinate in aqueous solution in the presence of hydrazine (U.S. Pat. No. 2,726,263). It has been found that increasing the amount of water in the hydrazine-containing reaction medium decreases the yield of TCH. The use of a waterfree solvent for hydrazine (e.g., methyl, ethyl, or propyl alcohol), however, does not increase the TCH yield. In the process disclosed in U.S. Pat. No. 2,726,263, the hydrazinium-dithiocarbazinate (obtained in the usual way through conversion of carbon disulfide with hydrazine hydrate), is heated in an aqueous hydrazine solution at approximately 95° C. for 1–2 hours under reflux. For each mole of hydrazinium-dithiocarbazinate, 1 to 3 moles of hydrazine are used. In a variation of this known process, carbon disulfide in aqueous solution with 3 to 6 times the amount of hydrazine is cooled and then heated. In both processes, the yield can be increased by repeatedly removing the TCH which forms during the course of the conversion from the reaction mixture. However, the yield is only 53.3% of theory.

It is also known to convert the hydrazinium-dithiocarbazinate thermally. Yields of approximately 70% of theory may be obtained (Petri, Z. Naturforsch, 16B, 769 (1961)) by such thermal decomposition.

In each of the above-described processes, any excess hydrazine must be recovered. Such recovery is costly, time consuming and troublesome due to the reactivity and instability of hydrazine.

U.S. Pat. No. 4,294,985 teaches that the mother liquor containing the excess hydrazine may be recycled instead of being recovered. However, recycling of the hydrazine-containing liquor creates new problems. More specifically, recycling results in the build up of impurities which can reduce the yield of TCH. Further, some of the hydrazine containing liquor must be purged from the system after each recycle resulting in loss of hydrazine.

It would therefore be advantageous to deVelop a process for producing TCH which did not require removal or recycling of excess of hydrazine but did produce TCH in high yield.

SUMMARY OF THE INVENTION

It is an object of the present invention to provide an improved process for producing TCH in high yield in which removal of excess hydrazine is not required.

It is also an object of the present invention to provide an improved process for producing TCH in which the mother liquor recovered from the reaction mixture is treated to react excess hydrazine present therein to form TCH.

It is a further object of the present invention to provide catalysts for a process for producing TCH in high yield which are inexpensive enough to discard or more stable and more easily recovered than hydrazine.

These and other objects which will be apparent to those skilled in the art are accomplished by reacting hydrazinium dithiocarbazinate (HDTC) with an amine (other than hydrazine) or a strong base, optionally in the presence of water.

DETAILED DESCRIPTION OF THE INVENTION

The present invention relates to a process in which thiocarbohydrazide (TCH) is produced by heating hydrazinium dithiocarbazinate (HDTC) in the presence of an amine other than hydrazine or a strong base at an elevated temperature, optionally in the presence of water. It is preferred that a small amount of a material which will retard formation of sulfur also be included in the reaction mixture. TCH precipitates as a solid and may be readily recovered from the mother liquor by any of a number of known techniques (e.g., filtration).

The mother liquor containing the hydrosulfide of the cation of the strong base may be further treated by adding more hydrazinium-dithiocarbazinate (HDTC) and any of the water or other material used to wash the precipitated TCH. This mixture is then heated. Hydrogen sulfide and the dithiocarbazinate of the cation of the strong base are formed and then recycled. Recycling improves the overall yield of TCH. The mother liquor may be recycled a number of times but recycling up to six times has been found to be most advantageous.

The reactions which occur during the process of the present invention may be summarized by the following equations. Where a strong base is used:

$$MX + H_2NNHCS\overset{\ominus}{S}H_3\overset{\oplus}{N}NH_2 \longrightarrow \quad (I)$$
$$(HDTC)$$

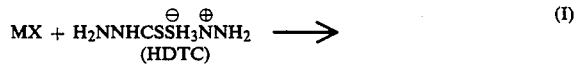

-continued

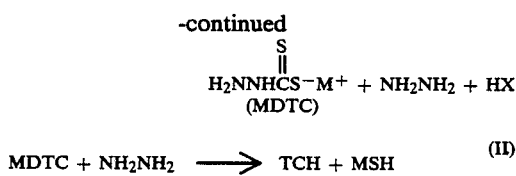

$$MDTC + NH_2NH_2 \longrightarrow TCH + MSH \quad (II)$$

$$MSH + HDTC \longrightarrow MDTC + H_2S + NH_2NH_2 \quad (III)$$

in which MX represents the strong base with M representing the cation and X representing the anion. Where an amine (B) is used:

$$B + H_2N-NHCS\overset{\ominus}{S}H_3\overset{\oplus}{N}NH_2 \longrightarrow \quad (IV)$$

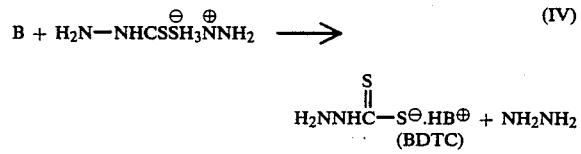

$$BDTC + NH_2NH_2 \longrightarrow TCH + BSH \quad (V)$$

$$BSH + HDTC \longrightarrow BDTC + H_2S + NH_2NH_2 \quad (VI)$$

The amount of water present during the reaction, if any, may be varied from about 0.5 to 1.0 and preferably about 0.75 times as much water by weight as HDTC.

The amine base used in the process of the present invention may be any amino compound other than hydrazine having a $pK_b$ value of from 3 to 6, preferably from 3 to 4. Examples of such amine bases include aliphatic amines such as triethylamine, tetramethylethylene-diamine, ammonia and diazabicyclooctane. The strong bases which may be used in the process of the present invention include inorganic materials having relatively high pH values (i.e., a pH greater than 10). Examples of such strong bases are the hydroxides of alkali metals such as sodium hydroxide and potassium hydroxide. Sodium hydroxide and tetramethylenediamine are particularly preferred bases.

The HDTC may be made by any of the methods known to those in the art. One relatively simple method for producing HDTC in quantitative yields is to react carbon disulfide with hydrazine in a molar ratio of 1:2 in an alcohol at 0°–30° C. Appropriate alcohols include methanol, ethanol and isopropanol. The HDTC is virtually insoluble in alcohols and may therefore be readily recovered by filtration, although the HDTC need not be isolated prior to use in the process of the present invention. If hydrazine hydrate is used to produce the HDTC, the water present in the alcohol upon completion of the reaction may be removed by distillation.

It is, of course, within the scope of the present invention to react carbon disulfide with hydrazine in the presence of the amine base or strong base to form HDTC (in accordance with equation (1)). The HDTC thus formed in a medium in which the base required in the practice of the process of the present invention is present may then be heated to form TCH directly.

Materials which suppress sulfur and ammonia formation may optionally be included in the reaction mixture. Inclusion of such materials in minor amounts is in fact, preferred. Examples of appropriate sulfur and ammonia suppressing agents include: mercaptoethanol and thioglycolic acid. Mercaptoethanol is particularly preferred. When included, these materials are advantageously used in a quantity of from 2 to 20 mole percent, preferably 2–5 mole percent and most preferably about 3 mole percent.

The TCH which precipitates as a solid in the reaction mixture is separated from the reaction mixture, washed (e.g., with a minimum amount of water) and dried. The remaining mother liquor may contain unreacted hydrazine, MSH or BSH, MDTC or BDTC, water and sulfur and ammonia suppressing agent, if used. HDTC (preferably as a dry solid) and any water used to wash the already-recovered TCH are then added to the mother liquor. The HDTC is added in a molar amount of from 0.5 to 1.0 times the molar amount of MSH or BSH present. More strong base or amine (other than hydrazine) may be added to the mother liquor, if necessary. However, such addition is usually unnecessary when the mother liquor is recycled.

The reactions represented by equations I and II and IV and V are carried out at a temperature of from 20° to 85° C., preferably from 50° to 80° C., most preferably from 65° to 75° C. for a total period of at least 10 hours, preferably from 10 to 40 hours and most preferably from 20 to 25 hours.

The reaction of equations III and VI is carried out at a temperature of from 0° to 40° C., preferably from 20° to 30° C., for at least 1 hour, preferably from 1–2 hours.

The process of the present invention is particularly advantageous in that yields of TCH (based on hydrazine) of greater than 80% and often greater than 85% are achieved without loss of hydrazine or the need for expensive steps to recover or remove hydrazine.

Having thus described our invention, the following Examples are given by way of illustration.

EXAMPLES

EXAMPLES 1-8

From 0.1–0.2 moles of various bases were reacted with 0.2 moles of HDTC in 8–30 ml water at 66°–75° C. for 12–68 hours. With the exception of Example 7, the mother liquor was not recycled. The specific reaction conditions, materials and yields of TCH are summarized in Table 1.

TABLE 1

| Example | Base | Amount Base (g) | Amount H₂O (ml) | Temp. °C. | Reaction Time (Hours) | Yield |
|---|---|---|---|---|---|---|
| 1 | None | — | — | — | — | 34% |
| 2 | Pyridine | 15 | 30 | 70 | 19 | 37% |
| 3 | Methylimidizole | 5 | 30 | 70 | 19 | 52% |
| 4 | Ammonia | 30 | 0 | 70 | 19 | 79% |
| 5 | Tetramethylenediamine | 5 | 25 | 75 | 19 | 80% |
| 6 | Sodium Hydroxide | 8 | 20 | 66 | 86 | 85% |
| 7 | Sodium Hydroxide* | 8 | 20 | 72 | 24 | 89% |
| 8 | Diazabicyclooctane | 5 | 30 | 60 | 60 | 68% |

*1 run 3 recycles of mother liquor (with 3 additions of 0.2 moles HDTC)

It may be readily appreciated from the data in Table 1 that aliphatic amines produce TCH in greater yields than heterocyclic amines. In general it has been found that the greater the basicity of the amine, the higher the yield of TCH.

Use of sodium hydroxide, an even stronger base, produced even higher yields of TCH. Recycling the mother liquor containing sodium hydroxide further increased the yield. These results with sodium hydroxide were surprising because it had been thought that NaDTC (formed during the reaction represented by equation I) might be inert to hydrazine because TCH would have to form by displacing the hydrosulfide ion (a strong base) with hydrazine (a weak base).

EXAMPLES 9–33

28 grams of HDTC were reacted in water with various amines at the various times and temperatures indicated in Table 2. The ammonia and sulfur suppressing agent mercaptoethanol was also included in some of the reaction mixtures in the amount indicated in Table 2. The mother liquor was not recycled unless indicated to the contrary in Table 2. The results are summarized in Table 2.

TABLE 2

| Example | ml $H_2O$ | Amine | Amount Amine | Time (hrs) | Temp °C. | ml ME | gm-TCH |
|---|---|---|---|---|---|---|---|
| 9 | 30 | Dabco | 7 gm | 43 | 70 | 0 | 12 |
| 10 | 30 | Dabco | 5 gm | 60 | 60 | 0 | 14.5 |
| 11 | 30 | Dabco | 5 gm | 19 | 75 | 0 | 13 |
| 12 | 30 | Dabco | 10 gm | 21 | 75 | 0 | 12.5 |
| 13 | 30 | Dabco | 5 gm | 20 | 70 | 3 | 8 |
| 14 | 30 | Dabco | 10 gm | 19 | 70 | 2 | 10.6 |
| 15 | 30 | Dabco | 10 gm | 19 | 70 | 0 | 12.8 |
| 16 | 30 | Dabco | 1 gm | 19 | 70 | 0 | 10.5 |
| 17 | 30 | Dabco | 5 gm | 21 | 75 | 3 | 12.3 |
| 18 | 30 | DMAP | 26 gm | 60 | 60 | 0 | 16.5 |
| 19 | 30 | DMAP | 6 gm | 21 | 75 | 0 | 14.5 |
| 20 | 30 | $N_2H_4$ | 15 gm | 19 | 70 | 2 | 19.0 |
| 21 | 14 | $N_2H_4$ | 5 gm | 19 | 70 | 0 | 19.4 |
| 22 | 30 | $N_2H_4$ | 1 gm | 4 + 16 | 80 + 70 | 2 | 10.7 |
| 23 | 30 | $N_2H_4$ | 5 gm | 21 | 75 | 3 | 17 |
| 24 | 30 | Pyridine | 15 gm | 19 | 70 | 0 | 7.8 |
| 25 | 30 | TEA | 10 gm | 21 | 75 | 0 | 13.8 |
| 26 | 30 | DMA | 6 gm | 19 | 70 | 0 | 9.9 |
| 27 | 30 | — | — | 19 | 70 | 3 | 7.3 |
| 28 | 30 | MID | 5 gm | 19 | 70 | 0 | 11.1 |
| 29 | 30 | TMEDA | 5 gm | 19 | 70 | 0 | 12.8 |
| 30 | 0 | $NH_4OH$ | 30 ml | 19 | 70 | 0 | 15.4[2] |
| 31 | 25 | TMEDA | 5 gm | 19 | 70 | 3 | 7.3 |
| 32 | ML of Ex. 31 | | | 6 + 16 | 80 + 70 | 1.5 | 20.3 |
| 33 | ML of Ex. 32 | | | 21 | 75 | 3 | 18.0 |

ME = mercaptoethanol
DABCO = diazabicyclooctane ($pK_b$ = 3.0, 8.7)
DMAP = dimethylaminopyridine ($pK_b$ = 4.3)
TEA = triethylamine ($pK_b$ = 3.35)
MID = methylimidazole
TMEDA = tetramethylenediamine
ML = mother liquor
[1] turned very dark
[2] A.I. 97% mpt 173–175° C.
[3] 45.6 g TCH out of 63.6 g - 71.7%. The ML gave 1.3 g sulfur and 3 g HDTC. Hydrazine accountability = 75.3%.

The data in Table 2 clearly indicate that mercaptoethanol retards decomposition of HDTC when reactions are run at higher temperatures and slows the conversion to TCH.

The weakest base (pyridine) gave the worst results.

EXAMPLE 34

28 gm HDTC (prepared by reacting carbon disulfide and hydrazine in methanol), 25 ml $H_2O$, 5 g tetramethylenediamine and 1.7 ml mercaptoethanol were combined in a 250 ml flask and heated at 75° C. for 19 hours. The white solid which formed was filtered off and washed with approximately 50 ml water. The wash was cooled, neutralized with acetic acid and filtered. The crystals which were filtered off were combined with the first crop of TCH collected to give a total TCH yield of 17 g (80%).

EXAMPLE 35

HDTC was prepared by stirring 8 moles (400.5 g) of hydrazine hydrate in 2 liters of methanol at 5° C. and then adding 4 moles (304.5 g) of carbon disulfide dropwise while maintaining the temperature below 10° C. This mixture was stirred for 45 minutes. The product was filtered off and washed with about 500 ml of methanol. The yield of HDTC was greater than 99%.

To 16 g of 50% NaOH (0.2M), 12 ml of water, and 1.5 ml of mercaptoethanol were added 28 g (0.2M) of the HDTC prepared above. The mixture was stirred and heated at 72° C. for 24 hours. The TCH was filtered and washed with 6 ml of water. To the mother liquor and wash were added 28 g of HDTC and 1.5 ml of mercaptoethanol. The mixture was heated again as before. The yield after 1 run and 3 recycles was 75 g (88%).

EXAMPLE 36

The procedure of Example 35 was repeated using HDTC, water, NaOH and mercaptoethanol in the quantities indicated below.

| | HDTC (gm) | $H_2O$ (gm) | NaOH (gm) | ME (gm) | TCH (gm) |
|---|---|---|---|---|---|
| First Run | 28 | 20 | 8 | 3 | 16.8 |
| First Recycle | 28 | 0 | 0 | 1.5 | 20.3 |
| Second Recycle | 28 | 0 | 0 | 1.5 | 17.9 |
| Third Recycle | 28 | 0 | 0 | 1.5 | 19.5 |

-continued

| | HDTC (gm) | H₂O (gm) | NaOH (gm) | ME (gm) | TCH (gm) |
|---|---|---|---|---|---|

The total yield of TCH was 75.4 g (87.9%).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of thiocarbohydrazide comprising reacting hydraziniumdithiocarbazinate with a strong base or an amine other than hydrazine at a temperature of from 20° to 85° C.

2. The process of claim 1 in which the strong base is sodium hydroxide.

3. The process of claim 1 in which the amine is tetramethylethylenediamine.

4. The process of claim 1 in which a compound that suppresses sulfur and ammonia formation is included in the reaction mixture.

5. The process of claim 4 in which the compound that suppresses sulfur and ammonia formation is mercaptoethanol.

6. The process of claim 5 in which the thiocarbohydrazide is separated from the reaction mixture thereby leaving a mother liquor.

7. The process of claim 6 in which hydarazinium dithiocarbazinate is added to the mother liquor and the resultant mixture is maintained at a temperature of from 65° to 75° C. to produce thiocarbohydrazide.

8. The process of claim 1 in which the thiocarbohydrazide is separated from the reaction mixture to leave a mother liquor to which hydrazinium dithiocarbazinate is added to form thiocarbohydrazide.

9. The process of claim 8 in which the thiocarbohydrazide formed in the mother liquor is separated off and the mother liquor is recycled.

* * * * *